(12) United States Patent
Bae et al.

(10) Patent No.: US 12,153,016 B2
(45) Date of Patent: Nov. 26, 2024

(54) POLLUTANT DETECTION DEVICES AND MONITORING SYSTEM HAVING THE SAME

(71) Applicant: Samsung Electronics Co., Ltd., Suwon-si (KR)

(72) Inventors: Dusik Bae, Hwaseong-si (KR); Euihyun Roh, Hwaseong-si (KR); Sangyoon Shin, Seoul (KR); Yongjun Ahn, Suwon-si (KR); Youngwook Kim, Seoul (KR); Mira Park, Hwaseong-si (KR); Hyunwoo Lee, Hwaseong-si (KR); Jeonghun Lim, Suwon-si (KR); Wonil Choi, Suwon-si (KR); Sojung Park, Bucheon-si (KR); Jiwoong Shin, Hwaseong-si (KR); Sangkyung Lee, Hwaseong-si (KR); Dongchol Choi, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 524 days.

(21) Appl. No.: 17/499,479

(22) Filed: Oct. 12, 2021

(65) Prior Publication Data
US 2022/0283119 A1     Sep. 8, 2022

(30) Foreign Application Priority Data
Mar. 5, 2021     (KR) .................. 10-2021-0029270

(51) Int. Cl.
*G08B 21/10*     (2006.01)
*G01N 1/14*     (2006.01)
(Continued)

(52) U.S. Cl.
CPC ............... *G01N 27/64* (2013.01); *G01N 1/14* (2013.01); *G01N 27/227* (2013.01); *G01N 27/27* (2013.01); *H01L 21/67253* (2013.01)

(58) Field of Classification Search
USPC .. 340/601, 525, 527, 538.16, 539.22, 539.3, 340/568.2, 579, 588, 630, 632, 636.19,
(Continued)

(56) References Cited

U.S. PATENT DOCUMENTS 5,473,810 A * 12/1995 Demarest ............. B65H 67/044
29/243.517
5,487,216 A *  1/1996 Demarest ................. B21G 1/08
53/118
(Continued)

FOREIGN PATENT DOCUMENTS

JP    H05306988 A    11/1993
JP    2001116680 A    4/2001
(Continued)

*Primary Examiner* — Daniel Previl
(74) *Attorney, Agent, or Firm* — Muir Patent Law, PLLC

(57) ABSTRACT

A detection device includes a transfer device to travel along a rail while gripping a carrier, and a detection structure mounted on the carrier. The detection structure includes a collector to suck in air, a detector connected to the collector, the detector including a plurality of sensors, a plurality of sensor control boards receiving electrical signals from the plurality of sensors, the plurality of sensor control boards generating, based on the electrical signals, type data and concentration data regarding pollutants included in the air sucked in by the collector, and a communication control board connected to the plurality of sensor control boards.

20 Claims, 9 Drawing Sheets

(51) Int. Cl.
  *G01N 27/22* (2006.01)
  *G01N 27/27* (2006.01)
  *G01N 27/64* (2006.01)
  *H01L 21/67* (2006.01)

(58) Field of Classification Search
  USPC .......................................... 340/691.6, 693.2
  See application file for complete search history.

(56) References Cited

U.S. PATENT DOCUMENTS

| | | |
|---|---|---|
| 6,658,917 B2 | 12/2003 | Kim et al. |
| 6,935,201 B2 | 8/2005 | Abraham et al. |
| 2008/0073993 A1* | 3/2008 | Sortore ............... F16C 32/0489 |
| | | 310/90.5 |
| 2009/0162467 A1* | 6/2009 | Uragami ................. B29C 43/36 |
| | | 425/139 |
| 2010/0327687 A1* | 12/2010 | Iannello ................... H02K 7/09 |
| | | 310/90.5 |
| 2011/0316376 A1* | 12/2011 | Sortore .................... H02K 7/09 |
| | | 310/90.5 |
| 2015/0084638 A1* | 3/2015 | Ishikawa ........... H01M 8/04649 |
| | | 324/426 |
| 2019/0110444 A1* | 4/2019 | Boehm .................. A01K 45/00 |
| 2019/0148196 A1 | 5/2019 | Lin et al. |
| 2020/0011791 A1* | 1/2020 | Kawasaki ............... G01N 21/64 |

FOREIGN PATENT DOCUMENTS

| | | |
|---|---|---|
| JP | 2005234625 A | 9/2005 |
| JP | 2007297196 A | 11/2007 |
| KR | 101507436 B1 | 4/2015 |

* cited by examiner

POLLUTANT DETECTION DEVICES AND MONITORING SYSTEM HAVING THE SAME

CROSS-REFERENCE TO THE RELATED APPLICATION

This application claims priority from Korean Patent Application No. 10-2021-0029270, filed on Mar. 5, 2021, in the Korean Intellectual Property Office, the disclosure of which is incorporated herein by reference in its entirety.

BACKGROUND

1. Field

The exemplary embodiments of the disclosure relate to a pollutant detection device and a monitoring system including the same.

2. Description of the Related Art

Various pieces of semiconductor equipment may be disposed on a semiconductor production line for manufacturing a semiconductor device. In order to prevent a semiconductor manufacturing process from being subjected to external environmental influences, a detection device and a monitoring system for sensing pollutants on the semiconductor production line are needed.

SUMMARY

The exemplary embodiments of the disclosure provide a detection device including a detection structure mounted on a transfer device.

The exemplary embodiments of the disclosure provide a monitoring system including a detection device.

A detection device according to exemplary embodiments of the disclosure may include a transfer device to travel along a rail while gripping a carrier, and a detection structure mounted on the carrier. The detection structure may include a collector to suck in air, a detector connected to the collector, the detector including a plurality of sensors, a plurality of sensor control boards to receive electrical signals from the plurality of sensors, the plurality of sensor control boards generating, based on the electrical signals, type data and concentration data regarding pollutants included in the air sucked in by the collector, and a communication control board connected to the plurality of sensor control boards.

A monitoring system according to exemplary embodiments of the disclosure may include detection devices to perform pollutant detection at points in a clean room, each of the detection devices including a transfer device to travel along a rail of a ceiling, and a detection structure mounted on the transfer device, a router to receive position data from the detection devices, a detection data server to receive detection data from the detection devices, an integrated database to receive the position data from the router and to receive the detection data from the detection data server, and a user interface to receive the position data and the detection data from the integrated database and to display the position data and the detection data in the form of two-dimensional image. The detection structure may include a collector to suck in air from the clean room, a detector connected to the collector, the detector including a plurality of sensors, a plurality of sensor control boards to receive electrical signals from the plurality of sensors, the plurality of sensor control boards generating, based on the electrical signals, type data and concentration data regarding pollutants included in the air sucked in by the collector, and a communication control board connected to the plurality of sensor control boards.

A detection device according to exemplary embodiments of the disclosure may include a transfer device to travel along a rail of a ceiling while gripping a carrier, and a detection structure mounted on the carrier, the detection structure including a lower structure, a middle structure, and an upper structure. The lower structure may include a battery, a pump, and a gas outlet connected to the pump. The middle structure may include a collector to suck in air from a clean room, a detector connected to the collector, and a plurality of sensor control boards to receive an electrical signal from the detector. The upper structure may include a communication control board connected to the plurality of sensor control boards. The detector may be connected to the pump, and the plurality of sensor control boards may generate, based on the electrical signal, type data and concentration data regarding pollutants included in the air sucked in by the collector.

BRIEF DESCRIPTION OF THE DRAWINGS

The above and other objects, features, and advantages of the inventive concept will become more apparent to those skilled in the art upon consideration of the following detailed description with reference to the accompanying drawings.

DETAILED DESCRIPTION OF EXEMPLARY EMBODIMENTS

Figure 1:
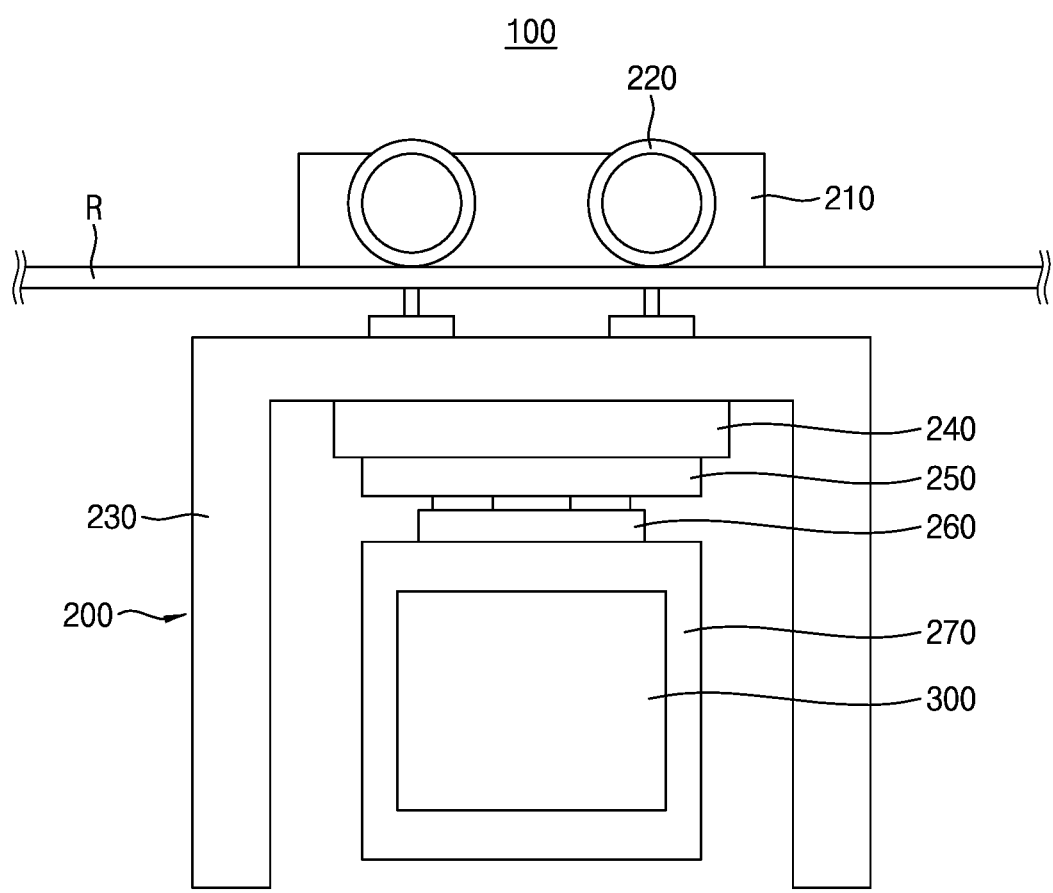
FIG. 1 illustrates a detection device according to an example embodiment of the inventive concepts.

FIG. 1 illustrates a detection device 100 according to an example embodiment of the inventive concepts.

Referring to FIG. 1, the detection device 100 may include a transfer device 200, a carrier 270 mounted on the transfer device 200, and a detection structure 300 disposed in the carrier 270. The transfer device 200 may move along a rail R fixedly coupled to a ceiling of a semiconductor production line or a clean room. The transfer device 200 may transfer the carrier 270 while moving along the rail R, and may be referred to as an overhead hoist transport (OHT). The rail R may be disposed adjacent to semiconductor processing equipment installed on the semiconductor production line or in the clean room. The rail R may extend in one direction. Generally, the transfer device 200 may be used to transfer substrates mounted on the carrier 270 to a load port disposed adjacent to the semiconductor processing equipment. The transfer device 200 according to the exemplary embodiment of the disclosure may also be used to transfer the detection structure 300 in order to detect pollutants adjacent to the semiconductor production line or in the clean room.

The transfer device 200 may include a travelling part 210, steering wheels 220, a housing 230, a moving part 240, a lifting part 250, and a gripping part 260. The travelling part 210 and the steering wheels 220 may be disposed on the rail R. The travelling part 210 may travel in a horizontal direction along the rail R in a state of contacting the rail R. The steering wheels 220 may be disposed at front and rear sides of the travelling part 210. The steering wheels 220 may rotate on the rail R, thereby moving the travelling part 210. For example, an actuator installed in the travelling part 210 may rotate the steering wheels 220.

The housing 230, the moving part 240, the lifting part 250 and the gripping part 260 may be disposed under the rail R. The housing 230 may be disposed under the travelling part 210, and may be fixed to the travelling part 210. A side surface of the housing 230 in a direction parallel to a travel direction of the transfer device 200 may be closed, and a side surface and a bottom surface of the housing 230 in a direction perpendicular to the travel direction of the transfer device 200 may be opened.

The moving part 240, the lifting part 250 and the gripping part 260 may be disposed inside the housing 230. The moving part 240 may be disposed at an inner top surface of the housing 230. The moving part 240 may horizontally move through the opened side surface of the housing 230. The lifting part 250 may be disposed under the moving part 240, and may be fixed to the moving part 240. The gripping part 260 may be disposed under the lifting part 250, and may be connected to the lifting part 250 via a lifting mechanism such as a belt, an arm or a bar. The gripping part 260 may grip the carrier 270, and may move upwards and downwards through the lifting mechanism.

Figure 2:
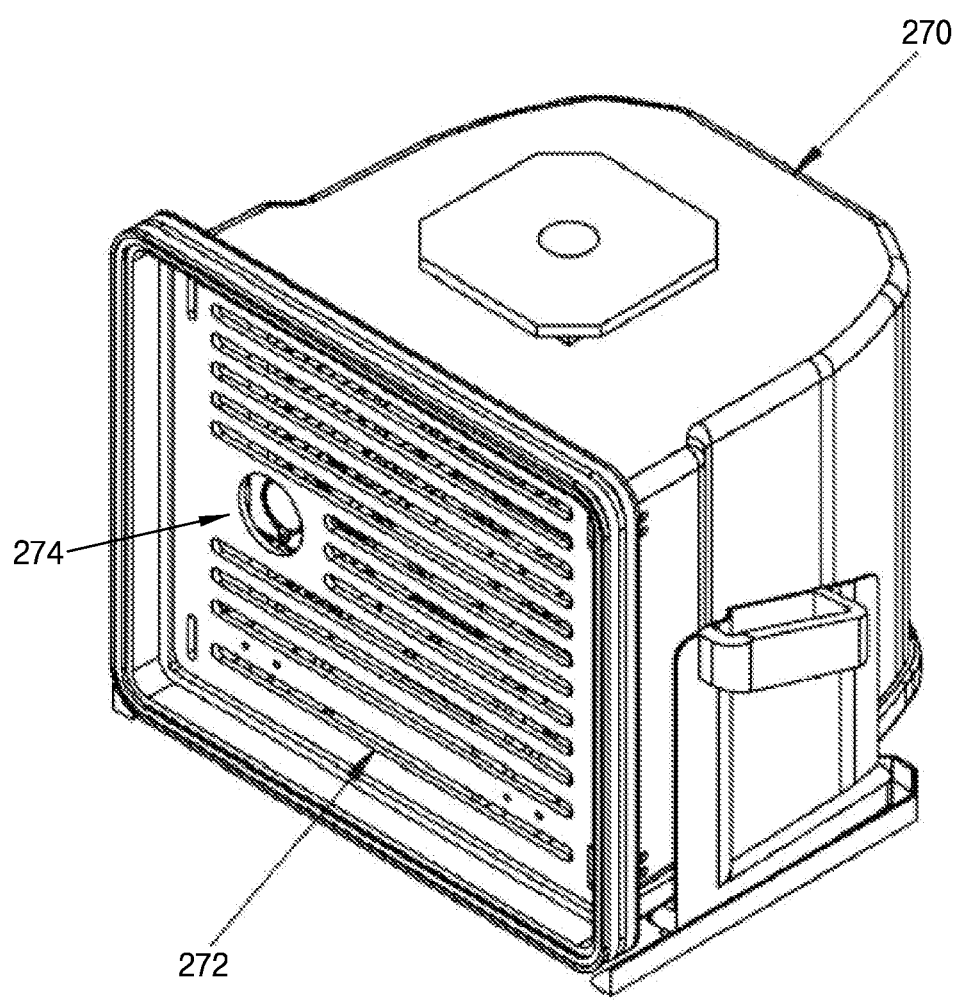
FIG. 2 is a perspective view of the carrier shown in FIG. 1.

FIG. 2 is a perspective view of the carrier 270 shown in FIG. 1.

Referring to FIG. 2, the carrier 270 may be a stacking device capable of stacking an object therein, such as a front opening unified pod (FOUP) or a front opening shipping box (FOSB). For example, the carrier 270 may have an opened front surface, closed side surfaces, and a closed rear surface. In an embodiment, the carrier 270 may include a lid 272 detachably attached to the front surface of the carrier 270. The lid 272 may include an opening 274 for sucking in air from a surrounding environment. The surrounding environment may include an area adjacent to the production line or in the clean room, as discussed above. In an embodiment, the lid 272 may be omitted.

Figure 3:
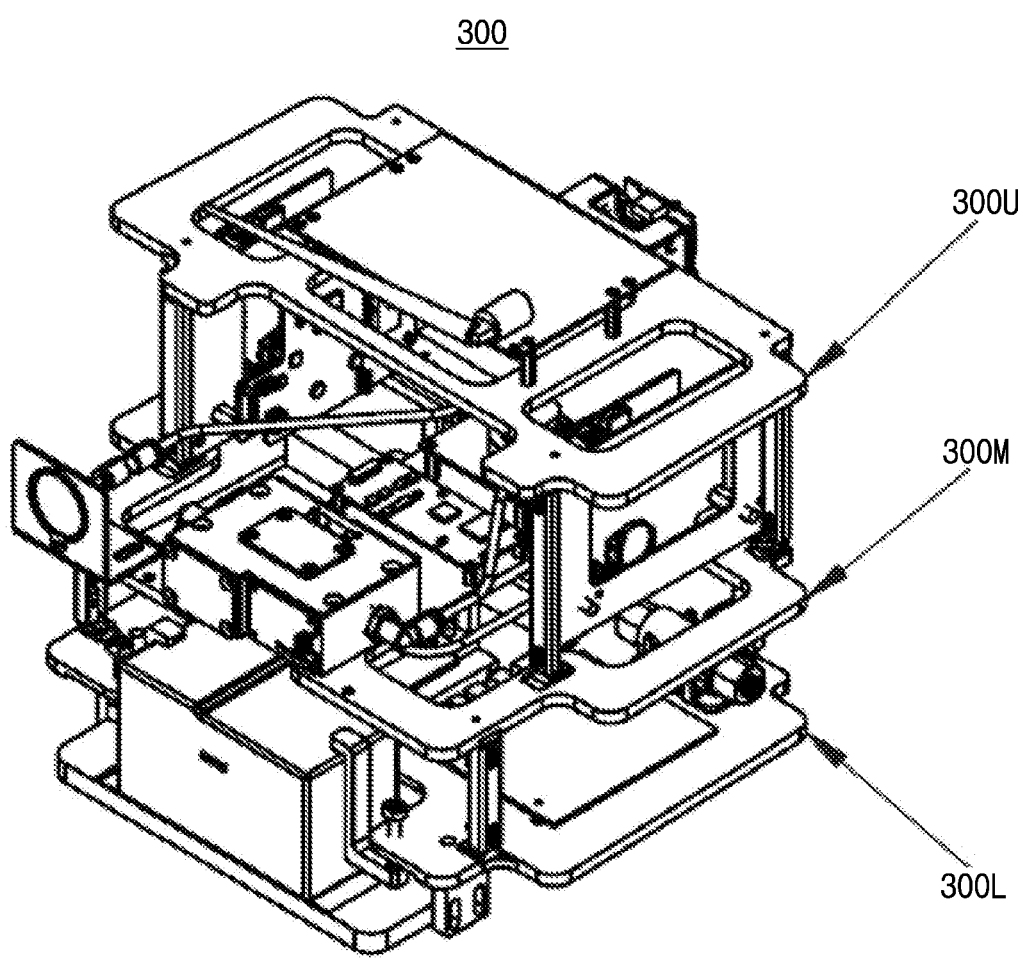
FIG. 3 is a perspective view of a detection structure according to an example embodiment of the inventive concepts.

FIG. 3 is a perspective view of a detection structure 300 according to an example embodiment of the inventive concepts.

Referring to FIG. 3, the detection structure 300 may have a structure in which one or more structures are stacked. For example, the detection structure 300 may include a lower structure 300L, a middle structure 300M, and an upper structure 300U. The detection structure 300 may be disposed inside the carrier 270, and may be transferred by the transfer device 200. As will be described later, the detection structure 300 may measure air in the surrounding environment, thereby detecting pollutants, and may collect image information using at least one camera or may send the collected image information to a detection data server.

Figure 4:
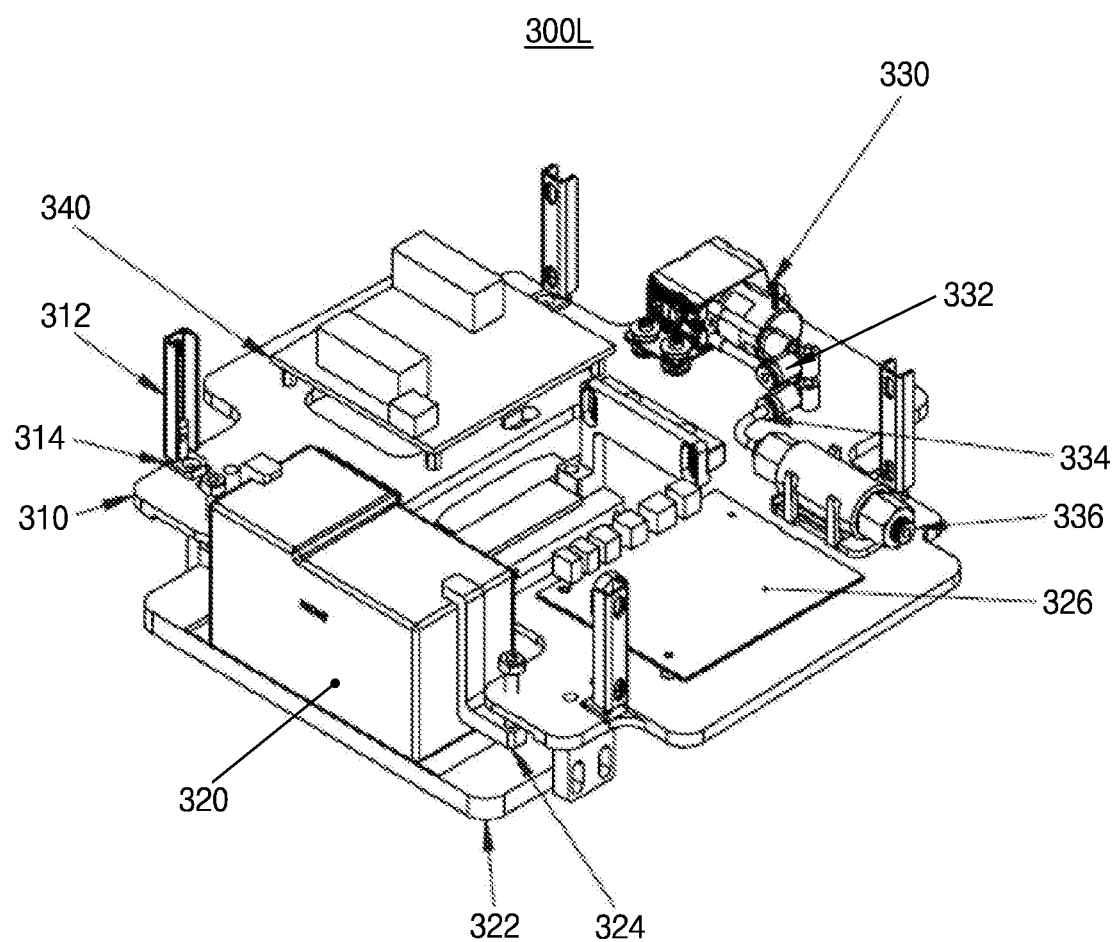
FIG. 4 is a perspective view of a lower structure of the detection structure according to an example embodiment of the inventive concepts.

FIG. 4 is a perspective view of a lower structure 300L of the detection structure according to an example embodiment of the inventive concepts.

Referring to FIG. 4, the lower structure 300L may include a lower frame 310, a battery 320, a battery support plate 322, a battery control board 326, a pump 330, a gas outlet 336, and a charging control board 340. The lower frame 310 may have a plate shape such that other constituent elements of the lower structure 300L may be installed thereon. The detection structure 300 may further include a fixing member 312 and a support 314. The fixing member 312 may be a structure extending vertically from a top surface of the lower frame 310, and may be disposed at a side surface of the lower frame 310. The fixing member 312 may support the middle structure 300M, and the support 314 may fix the fixing member 312 to the lower frame 310.

The battery 320 may be disposed on the battery support plate 322. The battery 320 may supply electric power to other constituent elements of the detection structure 300. In an embodiment, the battery support plate 322 may be a configuration separate from the lower frame 310. For example, the battery support plate 322 may be disposed below the lower frame 310, and may be fixedly coupled to the lower frame 310. The battery 320 may be disposed on the battery support plate 322. The detection structure 300 may further include battery fixing members 324 to fix the battery 320 to the battery support plate 322. The battery fixing members 324 may contact the battery support plate 322, and may be fixed to the lower frame 310 by screws or connecting pins.

The battery control board 326 may be disposed on the lower frame 310, and may be connected to the battery 320. The battery control board 326 may measure a charged state of the battery 320, and may send charged state data to a communication control board 520 which will be described later. As used herein, the term "board" may include a printed circuit board (PCB).

The pump 330 and the gas outlet 336 may be disposed on the lower frame 310. The pump 330 may include a pump inlet 332 and a pump outlet 334. The pump 330 may suck gas from the pump inlet 332, and may discharge the gas through the pump outlet 334. Although not shown, a pipe may be installed at the pump inlet 332, and may communicate with a detector of the middle structure 300M which will be described later. The pump outlet 334 may be connected to the gas outlet 336. The gas outlet 336 may externally exhaust gas discharged from the pump outlet 334. The gas outlet 336 may include a filter therein, and the filter may remove or filter out pollutants.

Figure 5:
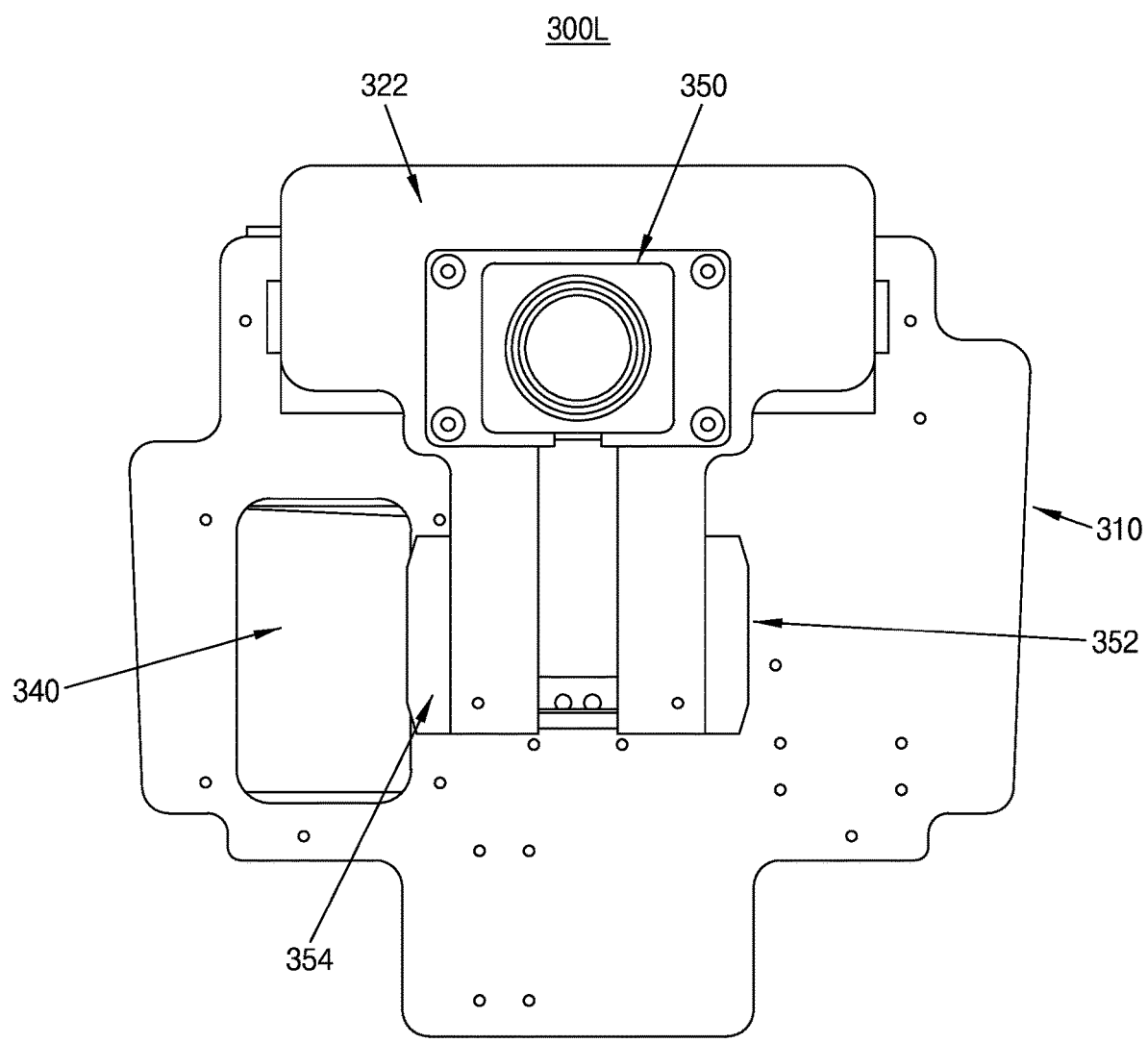
FIG. 5 is a bottom plan view of the lower structure according to an example embodiment of the inventive concepts.

FIG. 5 is a bottom plan view of the lower structure 300L according to an example embodiment of the inventive concepts.

Referring to FIGS. 4 and 5, the charging control board 340 may be disposed on the lower frame 310, and a charging coil 350, a magnet 352, and a magnet sensor 354 may be disposed under the lower frame 310. The charging control board 340 may control operation associated with charging of the battery 320. For example, the charging control board 340 may start or end wireless charging, and may determine whether or not the detection structure 300 is correctly positioned on a wireless charger. The charging control board 340 may be electrically connected to the charging coil 350 and the magnet sensor 354.

In an embodiment, the charging coil 350 may be attached to a bottom surface of the battery support plate 322. The charging coil 350 may have a structure in which a conductive wire is wound in a clockwise direction or a counterclockwise direction, and may have a circular shape, a rectangular shape, or an oval shape. The charging coil 350 may form a magnetic field in a direction perpendicular to a plane of the battery support plate 322, and may transmit electric power in a wireless manner. The charging coil 350 may be electrically connected to the charging control board 340 and the battery 320, and may charge the battery 320.

The magnet 352 and the magnet sensor 354 may be attached to a bottom surface of the lower frame 310. The magnet 352 and the magnet sensor 354 may be used to determine whether or not the detection structure 300 is positioned at a position suitable for execution of wireless charging. For example, for execution of wireless charging, the detection structure 300 should be positioned on a wireless charger of a wireless charging station, and the charging coil 350 should be positioned adjacent to a coil of the wireless charger. The magnet 352 and the magnet sensor 354 may be used to sense a position of a magnet disposed at the wireless charger, thereby determining whether or not the charging coil 350 is positioned adjacent to the coil of the wireless charger.

Figure 6:
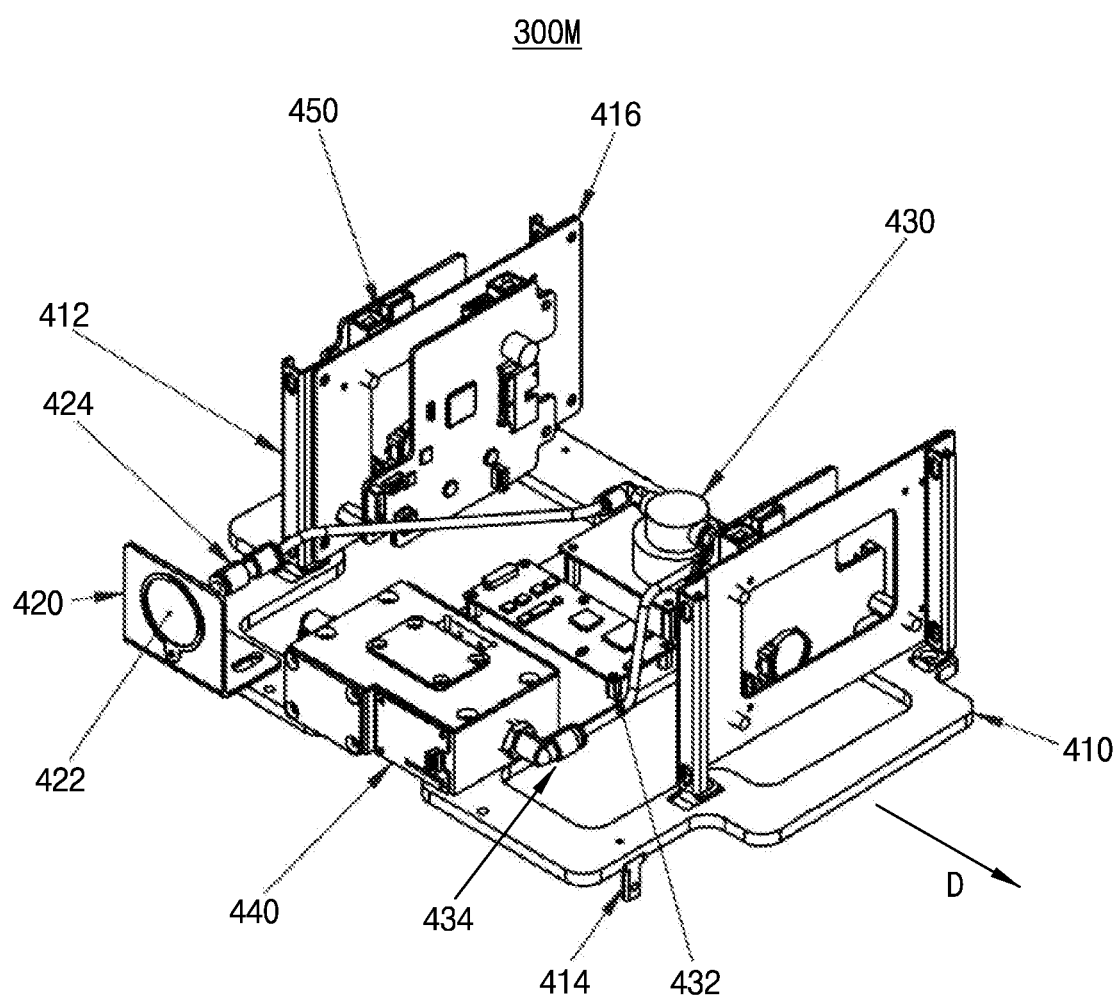
FIG. 6 is a perspective view of a middle structure of the detection structure according to an example embodiment of the inventive concepts.

FIG. 6 is a perspective view of a middle structure 300M of the detection structure according to an example embodiment of the inventive concepts.

Referring to FIG. 6, the middle structure 300M may include a middle frame 410, a collecting plate 420, a collector 422, a first pipe 424, a first detector 430, a first sensor control board 432, a second pipe 434, a second detector 440, and a second sensor control board 450. The middle frame 410 may have a plate shape such that other constituent elements of the middle structure 300M may be installed thereon. The middle structure 300M may further include a fixing member 412, a coupling pin 414, and a vertical frame 416. The fixing member 412 may be a structure extending vertically from the middle frame 410, and may support the upper structure 300U. The coupling pin 414 may extend downwards in a vertical direction from a side surface of the middle frame 410, and may be coupled to the fixing member 312 of the lower frame 300L. The vertical frame 416 may be a structure extending vertically from the middle frame 410, and may have a plate shape. The vertical frame 416 may be coupled to the fixing member 412.

The collecting plate 420 may fix the collector 422 to the middle frame 410. For example, the collecting plate 420 may have a bent structure having two faces, and one face of the collecting plate 420 may be fixed to the middle frame 410, whereas the other face of the collecting plate 420 may be fixed to the collector 422. Air in the surrounding environment may be sucked into the collector 422. The collector 422 may be exposed by the opening 274 of the lid 272 of the carrier 270. In an embodiment, the collector 422 may be disposed on the middle frame 410 at a rear side with reference to a travel direction D of the transfer device 200. As shown in FIG. 1, the housing 230 of the transfer device 200 may be closed at a face thereof parallel to the travel direction D, and a vortex flow or a turbulent flow may be formed by the housing 230 at a front side with reference to the travel direction D. Since the collector 422 according to the exemplary embodiment of the disclosure is disposed at a rear side with reference to the travel direction D, the detection structure 300 may more easily suck in air from the surrounding environment.

The first detector 430 may be connected to the collector 422 by the first pipe 424. The first detector 430 may include a chamber capable of receiving sucked in air, and a detection sensor disposed in the chamber, thereby being capable of detecting pollutants. In an embodiment, the first detector 430 may include a photo-ionization sensor (PID). The photo-ionization sensor may irradiate air sucked in by the collector 422 with light, thereby detecting pollutants. For example, pollutants may be ionized by ultraviolet light emitted from the photo-ionization sensor and, as such, the photo-ionization sensor may measure a current or a voltage of the ionized pollutants, thereby detecting the pollutants. In an embodiment, the photo-ionization sensor may detect total volatile organic compounds (TVOC).

Information as to the pollutants detected by the first detector 430 may be sent to the first sensor control board 432 in the form of an electrical signal. The first sensor control board 432 may determine the kind of pollutants and may calculate the concentration of the pollutants based on the electrical signal.

The second detector 440 may be connected to the first detector 430 by the second pipe 434. The second detector 440 may include a chamber capable of receiving sucked in air, and at least one detection sensor disposed in the chamber, thereby being capable of detecting pollutants. In an embodiment, the second detector 440 may include at least one of a metal oxide semiconductor (MOS) sensor and an electrochemical (EC) sensor.

The metal oxide semiconductor sensor may detect pollutants using oxidation/reduction reaction of a metal oxide. For example, the metal oxide semiconductor sensor may include a metal oxide therein, and may measure pollutants by measuring a variation in resistance of the metal oxide chemically reacting with the pollutants. In an embodiment, the metal oxide semiconductor sensor may detect pollutants, such as total volatile organic compounds (TVOC), hydrogen fluoride (HF), hydrogen chloride (HCl), and ammonia ($NH_3$).

The electrochemical sensor may include an electrolyte therein, and may detect a pollutant by measuring current of the electrolyte in which the pollutant is dissolved. In an embodiment, the second detector 440 may include at least one electrochemical sensor. For example, the second detector 440 may include a first electrochemical sensor, a second electrochemical sensor, and a third electrochemical sensor, each of which is capable of detecting HF, HCl, and $NH_3$.

Information as to the pollutants detected by the second detector 440 may be sent to the second sensor control boards 450 in the form of an electrical signal. In an embodiment, the second sensor control boards 450 may be attached to side surfaces of the vertical frames 416, respectively, and may be connected to corresponding sensors of the second detector 440, respectively.

The photo-ionization sensor may rapidly detect pollutants, as compared to other kinds of sensors such as a semiconductor sensor, an electrochemical sensor, etc. As shown in FIG. 6, the first detector 430 may be directly connected to the collector 422. That is, air sucked in by the collector 422 may be preferentially provided to the first detector 430 including the photo-ionization sensor and, as such, the detection structure 300 may more quickly detect pollutants.

Although the first detector 430 and the second detector 440 are shown in FIG. 6 as having configurations separate from each other, respectively, the exemplary embodiments of the disclosure are not limited thereto. In an embodiment, the first detector 430 may be integrated with the second detector 440. For example, a photo-ionization sensor, a metal oxide semiconductor sensor and an electrochemical sensor may be disposed in a single chamber. In another embodiment, the photo-ionization sensor, the metal oxide semiconductor sensor and the electrochemical sensor may be disposed in different chambers, respectively. In an embodiment, the detection structure 300 may further include sensors capable of measuring temperature and humidity.

Figure 7:
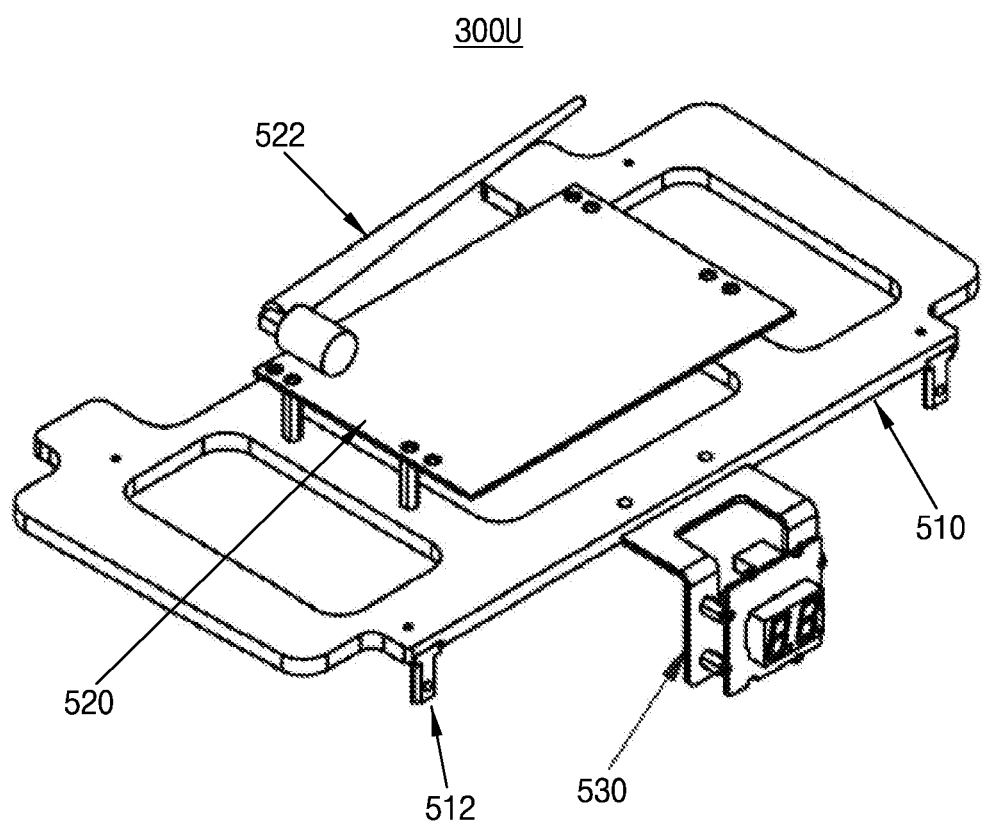
FIG. 7 is a perspective view of an upper structure of the detection structure according to an example embodiment of the inventive concepts.

FIG. 7 is a perspective view of an upper structure 300U of the detection structure according to an example embodiment of the inventive concepts.

Referring to FIG. 7, the upper structure 300U may include an upper frame 510, the communication control board 520, a communication module 522, and a display device 530. The upper frame 510 may have a plate shape such that other constituent elements of the upper structure 300U may be installed thereon. The upper structure 300U may further include a coupling pin 512. The coupling pin 512 may extend downwards in a vertical direction from a side surface of the upper frame 510, and may be connected to the middle structure 300M, thereby fixing the upper frame 510 to the middle structure 300M. For example, the coupling pin 512 may be coupled to the fixing member 412 of the middle structure 300M.

The communication control board 520 may be disposed on the upper frame 510. The communication control board 520 may be connected to the battery control board 326, the first sensor control board 432, and the second sensor control boards 450. The communication control board 520 may include a communication module 522, and may transmit data received from the battery control board 326, the first sensor control board 432, and the second sensor control boards 450 to a detection data server via the communication module 522. The communication module 522 may be connected to the detection data server through wired or wireless communication. For example, the communication module 522 may include an antenna, and may be connected to the detection data server in a wireless manner.

The display device 530 may be disposed at a side surface of the upper frame 510. The display device 530 may be connected to the battery control board 326, and may display a charged state and a remaining charge of the battery 320.

Figure 8:
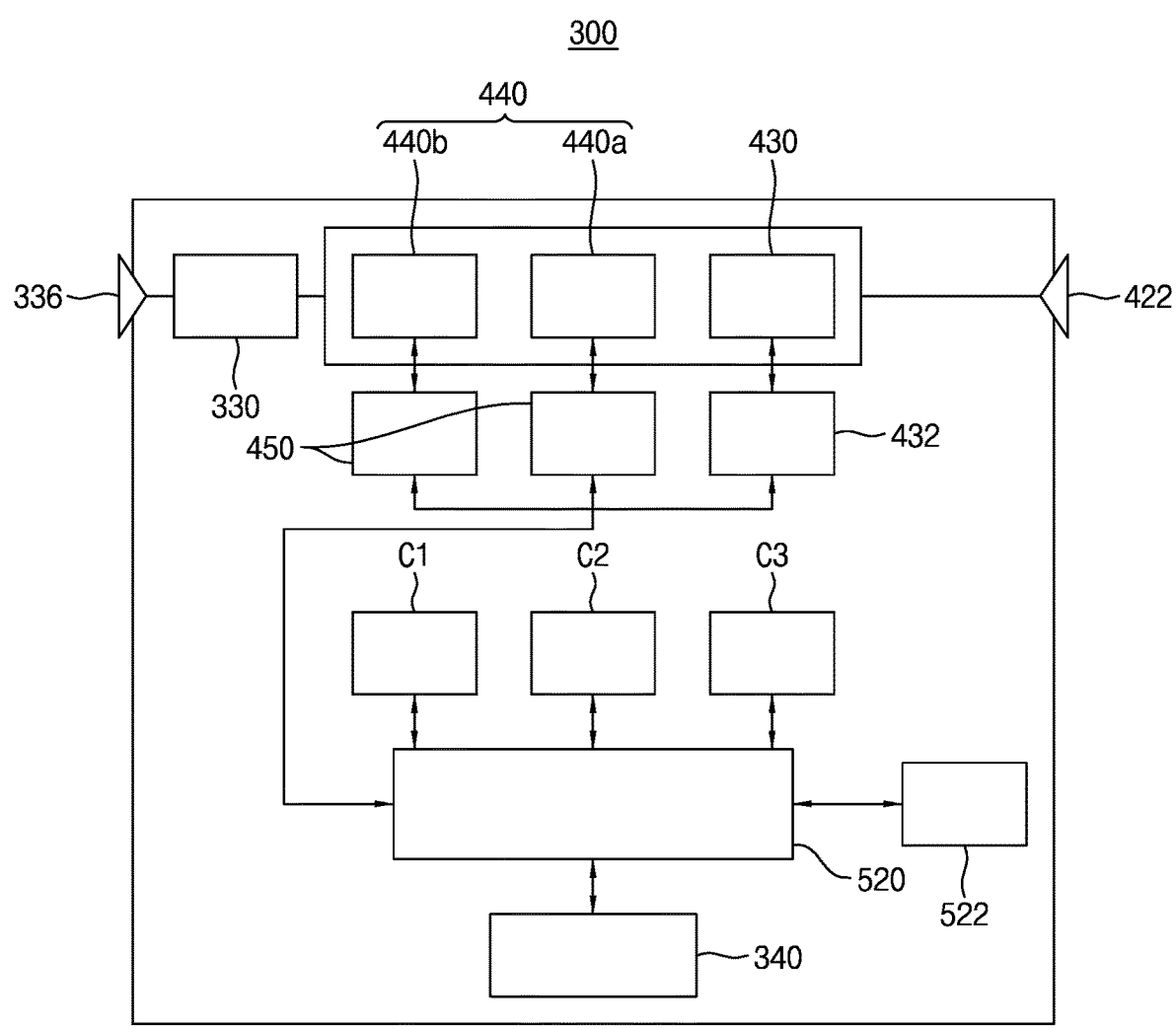
FIG. 8 is a block diagram for explaining operation of the detection structure.

FIG. 8 is a block diagram for explaining operation of the detection structure 300.

Referring to FIG. 8, the collector 422 may suck in air from the surrounding environment and, as such, may provide the sucked in air to detectors. The detectors may include the first detector 430 and the second detector 440. In an embodiment, as described above, the first detector 430 may include a photo-ionization sensor, and the second detector 440 may include a metal oxide semiconductor sensor 440a and an electrochemical sensor 440b. Air in the surrounding environment may be sent to the pump 330 via the first detector 430 and the second detector 440. The pump 330 may assist the collector 422 to suck in air. Thereafter, the air may be externally exhausted through the gas outlet 336. The gas outlet 336 may include a filter therein, and the filter may remove or filter out pollutants.

Sensor control boards may receive detection data from the detectors. For example, the first sensor control board 432 and the second sensor control board 450 may receive electrical signals from the first detector 430 and the second detector 440 as detection data, respectively, and may generate data as to the kind and concentration of pollutants based on the detection data. The first sensor control board 432 and the second sensor control board 450 may transmit data as to the kind and concentration of the pollutants to the communication control board 520. The detection device 100 according to the exemplary embodiment of the disclosure may include different kinds of sensors and, as such, may acquire more accurate characteristics and features regarding the pollutants, that in turn may be used to generate data regarding, for example, the kind and concentration of the pollutants. For example, the detection device 100 may include different kinds of sensors capable of detecting the same kind of pollutant and, as such, even when a false positive is generated from one of the sensors, it may be possible to enhance accuracy of data through comparison of positives of the remaining sensors, thereby preventing generation of errors.

The detection structure 300 may further include at least one camera. For example, in an embodiment, the detection structure 300 may include a first camera C1, a second camera C2, and a third camera C3. The first camera C1 may be a visual camera, the second camera C2 is a thermal camera, and the third camera C3 is a camera usable as both the visual camera and the thermal camera. The visual camera may sense a situation in the surrounding environment, and the thermal camera may sense abnormality of equipment or leakage of high-temperature gas. In an embodiment, the third camera C3 may be omitted. The first camera C1, the second camera C2 and the third camera C3 may transmit visual image information and thermal image data to the communication control board 520.

Since the detection structure 300 is mounted on the transfer device 200, as described above, the detection structure 300 may detect pollutants while moving along the rail R. Accordingly, it may be possible to check information regarding pollutants in the surrounding environment in real time, and to achieve early detection of pollutants.

The charging control board 340 may transmit data as to a charged state of the battery 320 to the communication control board 520 or may receive charging start and end commands from the communication control board 520.

The communication module 522 may receive data from the communication control board 520, and may transmit the data to the detection data server. The communication module 522 may be embodied in a wired or wireless manner. For example, the communication module 522 may include a wireless antenna.

Figure 9:
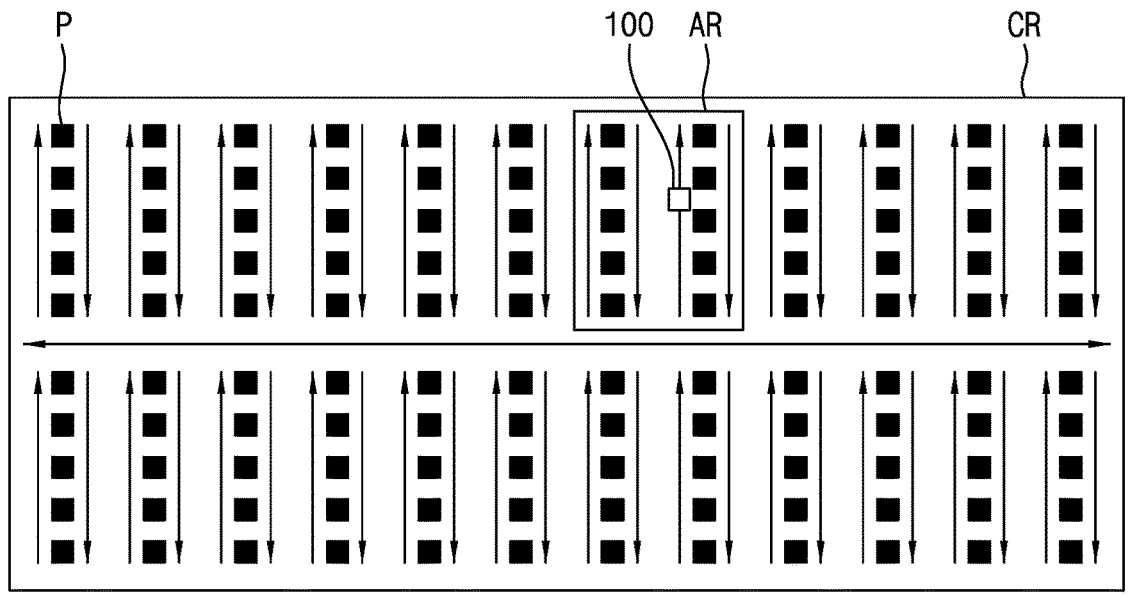
FIGS. 9 and 10 are conceptual diagrams for explaining a monitoring method according to an example embodiment of the inventive concepts.
Figure 10:
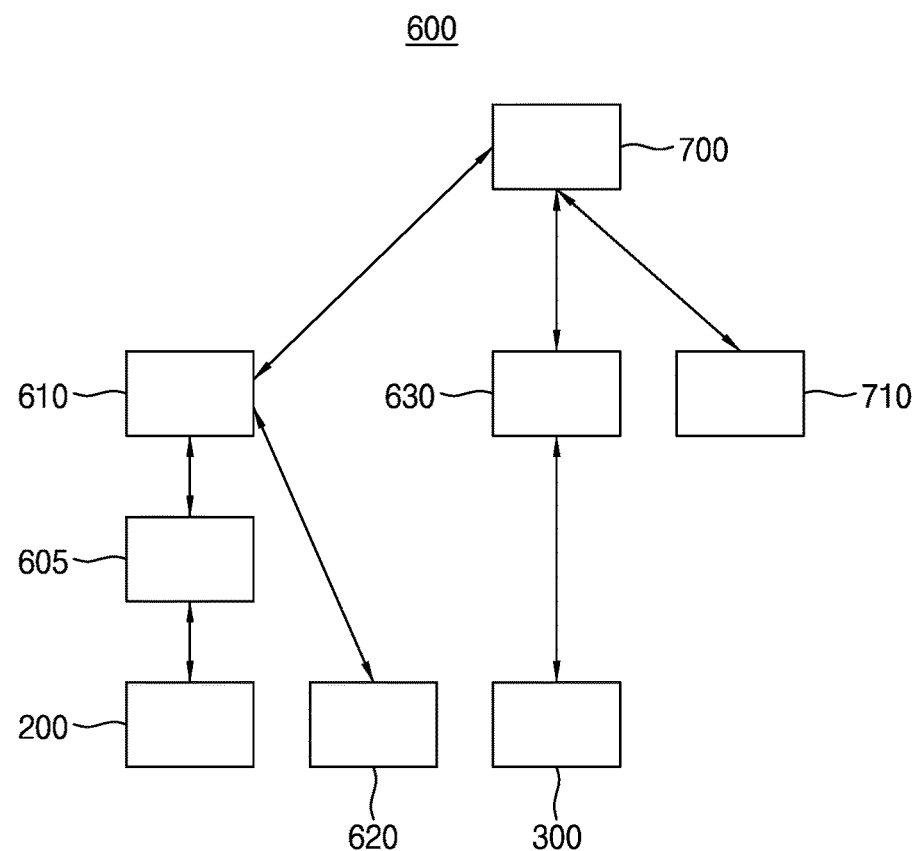

FIGS. 9 and 10 are conceptual diagrams for explaining a monitoring method according to an example embodiment of the inventive concepts. FIG. 9 is a plan view schematically showing a travel path of the detection device in a clean room. FIG. 10 schematically shows a pollutant monitoring method in the clean room.

Referring to FIG. 9, pieces of semiconductor processing equipment (not shown) may be disposed in a clean room CR, and the detection device 100 or the transfer device 200 may travel along paths (indicated by arrows) disposed adjacent to the pieces of semiconductor processing equipment. For example, a main path crossing the clean room CR may be disposed at a center of the clean room CR, and sub-paths may be configured to extend in a direction perpendicular to the main path. The rail R shown in FIG. 1 may be disposed along the paths.

The detection device 100 according to the exemplary embodiment of the disclosure may travel along the paths in the clean room CR, and may detect pollutants in the clean room CR at points P disposed to be spaced apart from one another. That is, the detection device 100 may acquire data as to a detection time, a detection position, the kind of pollutants and the concentration of pollutants. Devices, such as a clock may be included in the detection device 100 and may be utilized to acquire data as to the detection time. Devices, such as sensors configured to indoor positioning systems, the global position system (GPS), etc. may be included in the detection device 100 and may be utilized to acquire data as to the detection position. The data as to the detection time, the data as to the detection position, the data as to the kind of pollutants, and the data as to the concentration of pollutants may be referred to as "time data", "position data", "type data", and "concentration data", respectively.

In an embodiment, a single detection device 100 may sequentially perform detection for all points P, and may acquire time data, position data, type data, and concentration data for all points P in the clean room CR, without being limited thereto.

In an embodiment, a plurality of detection devices 100 may be disposed in the clean room CR, and each detection device 100 may perform detection at points P allocated therein. Since the plurality of detection devices 100 is used, it may be possible to check information on pollutants in the clean room CR in real time and, as such, may achieve early detection of pollutants.

In addition, as described with reference to FIG. 1, the carrier 270, in which the detection structure 300 is mounted, is movable upwards and downwards by the lifting part 250 and, as such, three-dimensional information on pollutants may be acquired. For example, the detectors may detect pollutants while moving in upward and downward directions, and the sensor control boards may generate three-dimensional concentration data. In an embodiment, the detection structure 300 may first acquire three-dimensional concentration data while moving in a vertical direction at a first point in the clean room CR, may then acquire three-dimensional concentration data of a second point after moving to the second point, and may subsequently move to a next point. Alternatively, a plurality of detection structures 300 may be used to detect pollutants at different heights. For example, an upper detection device, on which an upper detection structure is mounted, and a lower detection device, on which a lower detection structure is mounted, may be disposed in the clean room CR and, as such, the upper detection structure may detect pollutants at a higher level than the lower detection structure.

The detection devices 100 may monitor pollutants while traveling along designated paths, respectively. The designated paths may be defined by a plurality of rails R each extending in one of a plurality of directions. When pollutants of a predetermined level or more is detected in a particular area AR, it may be possible to more minutely detect pollutants in the particular area AR by concentrating the detection devices 100 around the particular area AR.

Referring to FIG. 10, a monitoring system 600 may include a transfer device controller 605, a router 610, a charging station 620, a detection data server 630, an integrated database 700, and a user interface 710. As used herein, the term "integrated database" refers to a database that unifies a variety of data from different sources.

The transfer device controller 605 may control movement of each transfer device 200. For example, the transfer device controller 605 may command the transfer device 200 to move to a particular point P in the clean room CR.

The router 610 may receive position data and time data as to all transfer devices 200 in the clean room CR from the transfer device controller 605, and may transmit the position data to the integrated database 700. Alternatively, the router 610 may transmit a command from the integrated database 700 to the transfer device controller 605. For example, when an abnormal situation is sensed at a particular area AR in the clean room CR, the integrated database 700 may send a command to the router 610 which may, in turn, send the command to the transfer device controller 605 and, as such, the transfer devices 200 may be concentratedly disposed in the particular area AR.

In addition, the router 610 may control a charging process of the transfer devices 200. Charging stations 620 capable of charging the detection structure 300 may be disposed in the clean room CR. In an embodiment, the charging stations 620 may be disposed at a buffer stage fixedly installed on a stocker and/or ceiling. The router 610 may receive charged state data of the detection structures 300, and may transmit the charged state data to the integrated database 700. When there is a detection structure 300 requiring charging, the integrated database 700 may transmit a charging command to the router 610, and the router 610 may then determine a charging station 620 to which the transfer device 200, on which the detection structure 300 to be charged is mounted, should move, taking into consideration the position of the transfer device 200, etc. The router 610 may subsequently transmit the command to the transfer device controller 605, thereby causing the transfer device 200 to move to the charging station 620.

The detection structures 300 may transmit detection data to the detection data server 630. For example, the detection structures 300 may transmit type data and concentration data to the detection data server 630. The detection data server 630 may transmit type data and concentration data of the detection structures 300 to the integrated database 700. Additional data, such as the time data and position data may also be transmitted to the router 610 by the transfer device 200. In an embodiment, the router 610 and the detection data server 630 may be integrated with each other, and the detection structure 200 may acquire all of position data, time data, type data and concentration data and may then transmit the acquired data to a server in which the router 610 and the detection data sever 630 are integrated.

The user interface 710 may receive position data, time data, type data and concentration data from the integrated database 700, may sort the received data in terms of items, and may display the sorted data, for example, in the form of a two-dimensional image. For example, the user interface 710 may display type data and concentration data for each point P in the clean room CR in a particular period of time. Alternatively, the user interface 710 may display type data and concentration data for a particular point P on a time period basis. In addition, when the detection devices 100 acquire three-dimensional concentration data, the user interface 710 may display three-dimensional information as to pollutants. For example, the user interface 710 may display type data and concentration data at each point P in a particular period of time in accordance with altitudes in the clean room CR.

In accordance with the exemplary embodiments of the disclosure, a detection device is movable by a transfer device and, as such, may quickly detect pollution in a surrounding environment. In addition, a monitoring system may display detection data in the form of a two-dimensional image.

While the embodiments of the disclosure have been described with reference to the accompanying drawings, it should be understood by those skilled in the art that various modifications may be made without departing from the scope of the disclosure and without changing essential features thereof. Therefore, the above-described embodiments should be considered in a descriptive sense only and not for purposes of limitation.

What is claimed is:

1. A detection device comprising:
a transfer device for traveling along a rail and gripping a carrier; and
a detection structure mounted on the carrier,
wherein the detection structure includes
a collector to suck in air,
a detector connected to the collector, the detector including a plurality of sensors,
a plurality of sensor control boards receiving electrical signals from the plurality of sensors, the plurality of sensor control boards generating, based on the electrical signals, type data and concentration data regarding pollutants included in the air sucked in by the collector, and
a communication control board connected to the plurality of sensor control boards.

2. The detection device according to claim 1, wherein the communication control board receives the type data and the concentration data from the plurality of sensor control boards.

3. The detection device according to claim 1, wherein the plurality of sensors includes a photo-ionization sensor, a metal oxide semiconductor sensor, and an electrochemical sensor.

4. The detection device according to claim 3, wherein:
the electrochemical sensor includes a first electrochemical sensor to detect hydrogen fluoride (HF), a second electrochemical sensor to detect hydrogen chloride (HCl), and a third electrochemical sensor to detect ammonia ($NH_3$);
the photo-ionization sensor detects total volatile organic compounds (TVOC); and
the metal oxide semiconductor sensor detects TVOC, HF, HCl, and $NH_3$,
wherein TVOC, HF, HCl, and $NH_3$ are pollutants.

5. The detection device according to claim 3, wherein the air sucked in by the collector is sent to the photo-ionization sensor before being sent to the electrochemical sensor and the metal oxide semiconductor sensor.

6. The detection device according to claim 1, wherein the detection structure further includes a pump connected to the detector, and a gas outlet connected to the pump.

7. The detection device according to claim 6, wherein the gas outlet further includes a filter to remove the pollutants.

8. The detection device according to claim 1, wherein:
the detection structure further includes a battery and a battery control board; and
the communication control board receives charged state data from the battery control board.

9. The detection device according to claim 1, wherein the transfer device further includes a lifting part to move the carrier in a vertical direction.

10. The detection device according to claim 9, wherein the plurality of sensor control boards generates three-dimensional concentration data based on the electrical signals.

11. A monitoring system comprising:
detection devices performing pollutant detection at points in a clean room, each of the detection devices including a transfer device traveling along a rail of a ceiling, and a detection structure mounted on the transfer device;
a router receiving position data from the detection devices;
a detection data server receiving detection data from the detection devices;
an integrated database receiving the position data from the router and receiving the detection data from the detection data server; and
a user interface receiving the position data and the detection data from the integrated database and displaying the position data and the detection data in the form of a two-dimensional image,
wherein the detection structure includes
a collector to suck in air from the clean room,
a detector connected to the collector, the detector including a plurality of sensors,
a plurality of sensor control boards receiving electrical signals from the plurality of sensors, the plurality of sensor control boards generating, based on the electrical signals, type data and concentration data regarding pollutants included in the air sucked in by the collector, and
a communication control board connected to the plurality of sensor control boards.

12. The monitoring system according to claim 11, wherein:
the router further receives time data from the detection devices;
the time data is sent to the user interface via the integrated database; and
the user interface displays detection data on a time period basis at at least one of the points in the clean room.

13. The monitoring system according to claim 11, wherein the detection data includes the type data and the concentration data.

14. The monitoring system according to claim 11, wherein:
the detection devices include a first detection device including a first detection structure, and a second detection device including a second detection structure;
the first detection structure is disposed at a higher level in the clean room than the second detection structure; and
the integrated database receives detection data from the first detection structure and the second detection structure via the detection data server.

15. The monitoring system according to claim 14, wherein the user interface displays detection data at at least one of the points in accordance with height information.

16. The monitoring system according to claim 11, wherein:
the integrated database sets at least one area in the clean room; and
the router transmits commands to move a plurality of the detection devices in the at least one area.

17. The monitoring system according to claim 11, further comprising:
charging stations disposed in the clean room,
wherein the integrated database receives charged state data from the detection devices.

18. The monitoring system according to claim 17, wherein the router transmits a command to move a first one of the detection devices to a corresponding one of the charging stations.

19. A detection device comprising:
a transfer device traveling along a rail of a ceiling and gripping a carrier; and
a detection structure mounted on the carrier, the detection structure including a lower structure, a middle structure, and an upper structure,
wherein the lower structure includes a battery, a pump, and a gas outlet connected to the pump, wherein the middle structure includes a collector to suck in air, a detector connected to the collector, and a plurality of sensor control boards receiving an electrical signal from the detector, wherein the upper structure includes a communication control board connected to the plurality of sensor control boards, and wherein the detector is connected to the pump, and the plurality of sensor control boards generate, based on the electrical signals, type data and concentration data regarding pollutants included in the air sucked in by the collector.

20. The detection device according to claim 19, wherein:

the detector includes a first detector including a photo-ionization sensor, and a second detector including a metal oxide semiconductor sensor and an electrochemical sensor; and the middle structure further includes a first pipe interconnecting the collector and the first detector, and a second pipe interconnecting the first detector and the second detector.

\* \* \* \* \*